(12) United States Patent
Shi et al.

(10) Patent No.: US 12,073,492 B2
(45) Date of Patent: Aug. 27, 2024

(54) METHOD AND SYSTEM FOR GENERATING ATTENUATION MAP FROM SPECT EMISSION DATA

(71) Applicant: YALE UNIVERSITY, New Haven, CT (US)

(72) Inventors: Luyao Shi, New Haven, CT (US); Chi Liu, Orange, CT (US); John Onofrey, Woodbridge, CT (US); Hui Liu, Beijing (CN)

(73) Assignee: YALE UNIVERSITY, New Haven, CT (US)

( * ) Notice: Subject to any disclaimer, the term of this patent is extended or adjusted under 35 U.S.C. 154(b) by 331 days.

(21) Appl. No.: 17/594,364

(22) PCT Filed: Apr. 17, 2020

(86) PCT No.: PCT/US2020/028672
§ 371 (c)(1),
(2) Date: Oct. 13, 2021

(87) PCT Pub. No.: WO2020/214911
PCT Pub. Date: Oct. 22, 2020

(65) Prior Publication Data
US 2022/0207791 A1 Jun. 30, 2022

Related U.S. Application Data

(60) Provisional application No. 62/836,167, filed on Apr. 19, 2019.

(51) Int. Cl.
*G06T 11/00* (2006.01)
*G06N 3/08* (2023.01)

(52) U.S. Cl.
CPC .............. *G06T 11/003* (2013.01); *G06N 3/08* (2013.01); *G06T 2207/10108* (2013.01); *G06T 2207/20081* (2013.01); *G06T 2207/20084* (2013.01)

(58) Field of Classification Search
CPC ......... G06T 11/003; G06T 2207/10108; G06T 2207/20081; G06T 2207/20084;
(Continued)

(56) References Cited

U.S. PATENT DOCUMENTS 8,611,628 B2    12/2013   Hu et al.
9,230,354 B2    1/2016    O'Connor et al.
(Continued)

FOREIGN PATENT DOCUMENTS

WO    2017223560 A1    12/2017
WO    2019051411 A1    3/2019

OTHER PUBLICATIONS

Beckwith et al, Detruncation of Attenuation Maps using Neural Networks, Worcester Polytechnic Institute, 2017, pp. 1-117. (Year: 2017).*

(Continued)

*Primary Examiner* — Aaron W Carter
*Assistant Examiner* — Kathleen M Broughton
(74) *Attorney, Agent, or Firm* — Welsh Flaxman & Gitler LLC

(57) ABSTRACT

A system for estimating attenuation coefficients from only single photon emission computed tomography (SPECT) emission data using deep neural networks includes an artificial neural network based upon machine learning system estimating attenuation maps for SPECT emission data, and associated attenuation correction method.

14 Claims, 11 Drawing Sheets

(58) Field of Classification Search
CPC .......... G06N 3/08; G06N 3/045; G06N 3/048; G06N 3/047; G06N 3/082; G06N 3/088; A61B 6/037

See application file for complete search history.

(56) References Cited

U.S. PATENT DOCUMENTS

2017/0323431 A1   11/2017   Sarkar et al.
2018/0061031 A1*   3/2018   Rong .................. A61B 6/5235

OTHER PUBLICATIONS

Mok et al, Initial Investigation of Using a Generative Adversarial Network for Denoising in Dual Gating Myocardial Perfusion SPECT, 2018, IEEE Nuclear Science Symposium and Medical Imaging Conference Proceedings, pp. 1-3. (Year: 2018).*
Shi et al, Deep learning-based attenuation map generation for myocardial perfusion SPECT, 2020, Eur J Nucl Med Mol Imaging (2020) 47: 2383-2395. (Year: 2020).*
Thejaswi et al, Deep-learning Method for Detruncation of Attenuation Maps, 2017, IEEE Nuclear Science Symposium and Medical Imaging Conference, pp. 1-3. (Year: 2017).*
Meikle et al, Transmission-Dependent Method for Scatter Correction in SPECT, 1994, J Nuc Med 35(2): 360-368. (Year: 1994).*
Ogawa et al, Practical Method for Position-Dependent Compton-Scatter Correction in Single Photon Emission CT, 1991, IEEE Transactions on Medical Imaging 10(3): 408-412. (Year: 1991).*
Feng et al, Use of three-dimensional gaussian interpolation in the projector/backprojector pair of iterative reconstruction for compensation of known rigid-body motion in SPECT, 2006, IEEE Transactions on Medical Imaging, 25(7): 838-844, 2006. (Year: 2006).*
Tadesse et al, Techniques for generating attenuation map using cardiac SPECT emission data only: a systematic review, 2019, Annals of Nuc Med (2019) 33: 1-13. (Year: 2019).*
Song et al, Low-dose Cardiac-gated SPECT studies using a Residual Convolutional Neural Network, 2019, IEEE 16th International Symposium on Biomedical Imaging, pp. 1-4. (Year: 2019).*
Collins English Dictionary definition for empirical evidence, accessed Dec. 8, 2023. (Year: 2023).*
Shi L et al, Deep learning-based attenuation map generation for myocardial perfusion SPECT, 2020, Eur J Nucl Med Mol Imaging (2020) 47: 2383-2395. (Year: 2020).*
Song C et al, Low-Dose Cardiac-Gated SPECT Studies Using a Residual Convolutional Neural Network, 2019, IEEE 16th International Symposium on Biomedical Imaging, pp. 1-5 (Year: 2019).*
Thejaswi, A et al., A Deep-Learning Method for Detruncation of Attenuation Maps, 2017 IEEE Nuclear Science Symposium and Medical Imaging Conference, URL: https://ieeexplore.ieee.org/abstract/document/8533039; DOI: 10.1109/NSSMIC.2017.8533039.
Shi, I., et al., Generating Attenuation Map for SPECT-only systems using Generative Adversarial Networks, The Journal of Nuclear Medicine; online: May 1, 2019 URL:http://jnm.snmjournals.org/content/60/supplement_1/572.short.
Deep learning-based attenuation map generation for myocardial perfusion SPECT Shi L, Onofrey JA, Liu H, Liu YH, Liu C. Deep learning-based attenuation map generation for myocardial perfusion SPECT. European Journal Of Nuclear Medicine And Molecular Imaging 2020, 47: 2383-2395. PMID: 32219492, DOI: 10.1007/s00259-020-04746-6.
Post-reconstruction attenuation correction for SPECT myocardium perfusion imaging facilitated by deep learning-based attenuation map generation Liu H, Wu J, Shi L, Liu Y, Miller E, Sinusas A, Liu YH, Liu C. Post-reconstruction attenuation correction for SPECT myocardium perfusion imaging facilitated by deep learning-based attenuation map generation. Journal Of Nuclear Cardiology 2021, 29: 2881-2892. PMID: 34671940, DOI: 10.1007/s12350-021-02817-1.
Deep-learning-based methods of attenuation correction for SPECT and PET Chen X, Liu C. Deep-learning-based methods of attenuation correction for SPECT and PET. Journal Of Nuclear Cardiology 2022, 30: 1859-1878. PMID: 35680755, DOI: 10.1007/s12350-022-03007-3.
Direct and indirect strategies of deep-learning-based attenuation correction for general purpose and dedicated cardiac SPECT Chen X, Zhou B, Xie H, Shi L, Liu H, Holler W, Lin M, Liu YH, Miller EJ, Sinusas AJ, Liu C. Direct and indirect strategies of deep-learning-based attenuation correction for general purpose and dedicated cardiac SPECT. European Journal Of Nuclear Medicine And Molecular Imaging 2022, 49: 3046-3060. PMID: 35169887, PMCID: PMC9253078.
Data Management and Network Architecture Effect on Performance Variability in Direct Attenuation Correction via Deep Learning for Cardiac Spect: A Feasibility Study, Torkaman M, Torkaman M, Yang J, Shi L, Wang R, Miller EJ, Sinusas AJ, Liu C, in IEEE Transactions on Radiation and Plasma Medical Sciences, vol. 6, No. 7, pp. 755-765, Sep. 2022, doi: 10.1109/TRPMS.2021.3138372. keywords: {Single photon emission computed tomography; Attenuation;Deep learning; Generative adversarial networks; Task.
CT-free attenuation correction for dedicated cardiac SPECT using a 3D dual squeeze-and-excitation residual dense network Chen X, Zhou B, Shi L, Liu H, Pang Y, Wang R, Miller EJ, Sinusas AJ, Liu C. CT-free attenuation correction for dedicated cardiac SPECT using a 3D dual squeeze-and-excitation residual dense network. Journal Of Nuclear Cardiology 2021, 29: 2235-2250. PMID: 34085168, DOI: 10.1007/s12350-021-02672-0.
Direct Attenuation Correction Using Deep Learning for Cardiac Spect: A Feasibility Study Yang J, Shi L, Wang R, Miller EJ, Sinusas AJ, Liu C, Gullberg GT, Seo Y. Direct Attenuation Correction Using Deep Learning for Cardiac Spect: A Feasibility Study. Journal Of Nuclear Medicine 2021, 62: 1645-1652. PMID: 33637586, PMCID: PMC8612332, Doi: 10.2967/jnumed.120.256396.
DuDoCFNet: Dual-Domain Coarse-to-Fine Progressive Network for Simultaneous Denoising, Limited-View Reconstruction, and Attenuation Correction of Cardiac SPECT Chen, X., Zhou, B., Guo, X., Xie, H., Liu, Q., Duncan, J. S., . . . & Liu, C. (2024). IEEE Transactions on Medical Imaging.
Cross-Vender, cross-tracer, and cross-protocol deep transfer learning for attenuation map generation of cardiac SPECT Chen X, Pretorius P, Zhou B, Liu H, Johnson K, Liu YH, King MA, Liu C. Cross-vender, cross-tracer, and cross-protocol deep transfer learning for attenuation map generation of cardiac SPECT. Journal Of Nuclear Cardiology 2022, 29: 3379-3391. PMID: 35474443, DOI: 10.1007/s12350-022-02978-7.

* cited by examiner

METHOD AND SYSTEM FOR GENERATING ATTENUATION MAP FROM SPECT EMISSION DATA This invention was made with an American Heart Association award 18PRE33990138 and government support under HL123949 awarded by National Institutes of Health. The government has certain rights in the invention.

BACKGROUND OF THE INVENTION

1. Field of the Invention

The invention relates to estimating attenuation coefficients and attenuation maps (ATTMAP) from single photon emission computed tomography emissions and, where necessary, providing for attenuation correction for SPECT imaging.

2. Description of the Related Art

Single photon emission computed tomography (SPECT) is a non-invasive imaging procedure that can provide radiotracer distribution images of the patient body by detecting gamma-ray photons. SPECT plays an important role in the clinical diagnosis of cardiovascular, oncological, and neurological disease. In order to perform qualitative, quantitative, or semi-quantitative analysis for SPECT, accurate attenuation correction is essential.

Studies showed that attenuation correction can reduce ambiguity in diagnosis. Scans being interpreted as "normal" increased from 45% to 72% after the addition of attenuation correction, and confidence (total scans that are unequivocal) went from 57% to 80% after the addition of attenuation correction [van Dijk J, Mouden M, Ottervanger J, van Dalen J, Knollema S, Slump C, et al. Value of attenuation correction in stress-only myocardial perfusion imaging using CZT-SPECT. Journal of Nuclear Cardiology. 2017; 24:395-401]. Attenuation correction can also increase diagnostic positive predictive values (PPV). Use of computer tomography (CT) for attenuation correction led to significant increases in "true positive" results and significant decreases in "false positive" results as confirmed by invasive coronary angiography (ICA), significantly increasing PPV from 0.28 to 0.76 [Patchett N D, Pawar S, Sverdlov A, Miller E J. Does Improved Technology in SPECT Myocardial Perfusion Imaging Reduce Downstream Costs? An Observational Study. International Journal of Radiology and Imaging Technology. 2017; 3. doi:10.23937/2572-3235.1510023]. Moreover, more accurate diagnosis with attenuation corrected SPECT (SPECT/CT) leads to significant reduction in preventable diagnostic services of about $1,500 per patient/year by reducing unnecessary downstream invasive angiography procedures.

Many recent hybrid SPECT systems are equipped with a CT scanner that can be used to measure photon attenuation. However, these systems are substantially more expensive than SPECT-only systems and often require larger imaging rooms and additional room lead shielding. Currently, standalone SPECT systems still occupy the majority (around 80%) of the SPECT market share and these systems are susceptible to attenuation artifacts. Moreover, the use of CT scans also increases radiation doses to patients and significant artifacts could appear due to mismatches between the SPECT and CT scans as a result of respiratory motion, cardiac motion, and patient motion.

With the foregoing in mind, efforts have been made on estimating the attenuation map only using the SPECT emission data. Existing techniques for estimating the attenuation map from SPECT emission data can be classified into two categories. The first category includes segmentation-based methods that use either the photopeak or the scatter data to reconstruct the attenuation images [Pan, T.-S., King, M. A., Luo, D.-S., Dahlberg, S. T., et al.: Estimation of attenuation maps from scatter and photopeak window single photon-emission computed tomographic images of technetium 99m-labeled sestamibi, Journal of Nuclear Cardiology 4, 42-51 (1997); Zaidi, H., Hasegawa, B.: Determination of the attenuation map in emission tomography, Journal of Nuclear Medicine 44, 291-315 (2003)]. A coarse attenuation map can be obtained by segmenting different regions in SPECT images and assigning pre-defined attenuation coefficients. However, these methods are based on the inaccurate assumption that tissues have uniform attenuation coefficients. They also rely on segmentation by humans which is operator-dependent, time-consuming, and challenging in clinical workflow. The second category of methods is model-based methods that estimate the attenuation coefficients directly from the emission data [Jha, A. K., Zhu, Y., Clarkson, E., Kupinski, M. A., et al.: Fisher information analysis of list-mode SPECT emission data for joint estimation of activity and attenuation distribution, arXiv preprint arXiv:1807.01767 (2018); Cade, S. C., Arridge, S., Evans, M. J., Hutton, B. F.: Use of measured scatter data for the attenuation correction of single photon emission tomography without transmission CT scanning, Medical physics 40, 082506 (2013)]. However, these models either neglect scattered photons or only consider photons that have been scattered once [Jha, A. K., Zhu, Y., Clarkson, E., Kupinski, M. A., et al.: Fisher information analysis of list-mode SPECT emission data for joint estimation of activity and attenuation distribution, arXiv preprint arXiv:1807.01767 (2018)], which are not very accurate. These methods also suffer from high computation time and were only applied on 2D SPECT systems.

In recent years, deep learning-based approaches have been proposed to estimate images of one modality from another [Nie, D., Trullo, R., Lian, J., Wang, L., et al.: Medical image synthesis with deep convolutional adversarial networks, IEEE Transactions on Biomedical Engineering 65, 2720-2730 (2018); Hwang, D., Kang, S. K., Kim, K. Y., Seo, S., et al.: Generation of PET attenuation map for whole-body time-of-flight 18F-FDG PET/MRI using a deep neural network trained with simultaneously reconstructed activity and attenuation maps, Journal of Nuclear Medicine jnumed, 118.219493 (2019); Han, X.: MR-based synthetic CT generation using a deep convolutional neural network method, Medical physics 44, 1408-1419 (2017)]. Particularly, initial success was obtained for the task of generating attenuation maps for nuclear images. In "MR-based synthetic CT generation using a deep convolutional neural network method," convolutional neural networks were used to convert magnetic resonance imaging (MRI) images to attenuation CT images for PET/MRI systems. In "Generation of PET attenuation map for whole-body time-of-flight 18F-FDG PET/MRI using a deep neural network trained with simultaneously reconstructed activity and attenuation maps," Hwang et al. proposed to predict the CT-attenuation maps from PET data alone. Nonetheless, no attempt was reported on attenuation map synthesis for SPECT.

SUMMARY

According to a first aspect there may be provided a system for estimating attenuation coefficients and/or attenuation maps (ATTMAP) from only single photon emission computed tomography (SPECT) emission data using deep neural networks. The system includes a machine learning system based upon artificial neural networks for estimating attenuation maps for SPECT emission data.

In some embodiments the machine learning system includes a generator network estimating attenuation maps for SPECT emission data and a discriminator network enforcing output of the generator network to be consistent with a ground truth attenuation map.

In some embodiments the generator network is trained.

In some embodiments the generator network is trained with Generative Adversarial Network (GAN) training.

In some embodiments the generator network is trained with an Adam optimizer.

In some embodiments the discriminator network is trained.

In some embodiments the discriminator network is trained with an Adam optimizer.

In some embodiments the generator network is a deep convolutional neural network.

In some embodiments the discriminator network is a deep convolutional neural network.

In some embodiments the ground truth attenuation map is generated based upon empirical evidence.

In some embodiments the SPECT emission data includes images reconstructed from photopeak window and/or scatter window.

In some embodiments the images reconstructed from the photopeak window and the scatter window are concatenated as a multi-channel image and fed into a generator network.

In another aspect there may be provided a method for generating attenuation maps and performing associated attenuation correction from SPECT emission data. The method incudes generating an attenuation map from a NAC (non-attenuation corrected) SPECT image dataset (photopeak window or both photopeak combined with scatter windows) through deep learning, estimating attenuated projection data via forward projecting the NAC SPECT image without incorporating the attenuation map, and reconstructing an AC (attenuation corrected) SPECT image from the estimated attenuated projection data using iterative reconstruction with attenuation correction by incorporating the attenuation map generated by deep learning.

Additional advantages of the embodiments will be set forth in part in the description which follows, and in part will be understood from the description, or may be learned by practice of the invention. The advantages will be realized and attained by means of the elements and combinations particularly pointed out in the appended claims.

DESCRIPTION OF THE EMBODIMENTS

Figure 1:
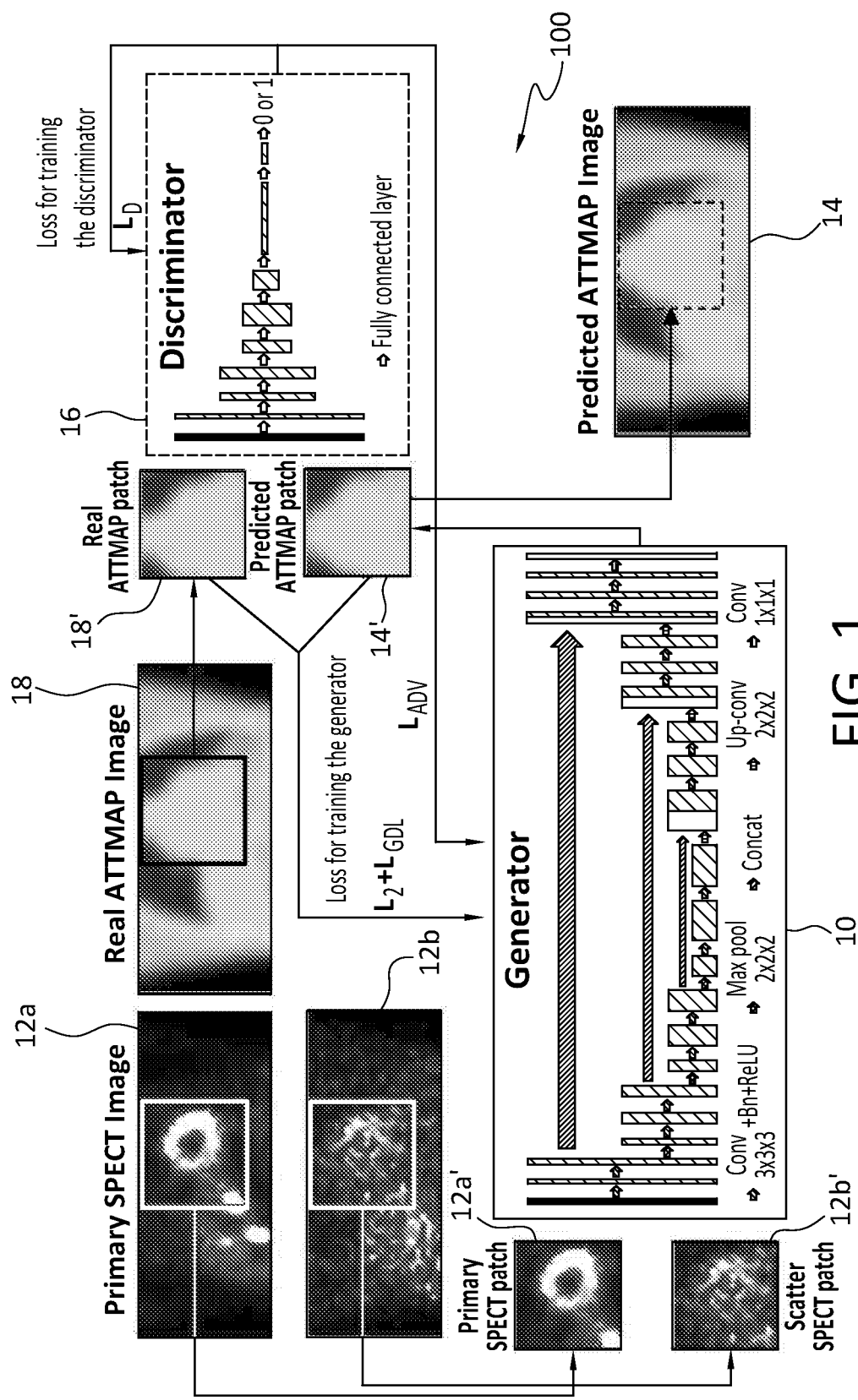
FIG. 1 is a schematic of the present method and system for estimating attenuation coefficients and attenuation maps (ATTMAP) from only single photon emission computed tomography (SPECT) emission data.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring now to the various drawings, disclosed are a method and system for estimating attenuation coefficients and attenuation maps (ATTMAP) from only single photon emission computed tomography (SPECT) emission data using deep neural networks and performing attenuation correction, without requiring additional computed tomography (CT) or other transmission images. As those skilled in the art will appreciate, the terms attenuation coefficient and attenuation map are related terms and are often used interchangeably since attenuation coefficients are basically the values used in creating the attenuation maps. In accordance with one embodiment of the present invention, both images reconstructed from photopeak windows and scatter windows are fed into deep neural networks to generate synthetic attenuation map images. In addition, images from a single energy window, either photopeak window or scatter window, can also be fed into deep neural networks to generate synthetic attenuation coefficient images.

As those skilled in the art will certainly appreciate, SPECT is a non-invasive imaging procedure that provides radiotracer distribution images of a patient's body by detecting gamma photons. SPECT plays an important role in the clinical diagnosis of cardiovascular, oncological and neurological disease. In order to perform qualitative, quantitative, or semi-quantitative analysis for SPECT, accurate attenuation correction is essential.

As those skilled in the art will further appreciate, and as discussed above, hybrid SPECT/CT systems equipped with transmission CT scanners can provide direct measurement of photon attenuation but are substantially more expensive than conventional SPECT systems and often require larger imaging rooms, additional shielding, and relatively complicated acquisition protocols. Many current SPECT-only systems do not support transmission or CT scanning and therefore are susceptible to attenuation artifacts. Where available, the use of transmission CT scanning also increases radiation doses to the patient and significant artifacts could occur due to mismatches between the SPECT and transmission CT scans as a result of patient motion. Due to all these reasons, the present method and system have been developed for estimating attenuation coefficients that are then used in creating an attenuation map (ATTMAP) directly from SPECT emission data using deep neural networks. The attenuation map may then be used in image reconstruction of the SPECT emission data to produce accurate images of the patient's body.

The present method and system for estimating attenuation coefficients from only SPECT emission data uses a deep learning-based model for estimating attenuation maps directly from SPECT emission data. Briefly, 3D (three-dimensional) models are developed using a generator network 10, which in accordance with the present invention is a deep convolutional neural network (CNN) with Generative Adversarial Network (GAN) training, to estimate attenuation maps for SPECT directly and solely from the SPECT emission data 12$a$, 12$b$. As demonstrated below, qualitative and quantitative analysis demonstrates that the present method and system is capable of generating accurate attenuation maps. Evaluations on real human data showed that the present method produces attenuation maps that are consistent with CT-based attenuation maps, and provides accurate attenuation correction for SPECT images. The attenuation maps produced in accordance with the present invention are then used to correct raw SPECT data or SPECT images reconstructed without attenuation correction to produce highly accurate body images based solely upon SPECT emission data.

In practice, once the deep convolutional neural network (CNN) is fully trained using GAN techniques, the deep convolutional neural network (CNN) is used in conjunction with SPECT imaging to produce attenuation maps that are applied in conjunction with generated emissions data to produce accurate body images. As those skilled in the art appreciate, GAN techniques refer to machine learning systems wherein two neural networks compete with each in a manner generating new data with the same statistics as the training set.

Referring to FIG. 1, a system 100 in accordance with the present invention is disclosed that employs a machine learning system based upon artificial neural networks to estimate attenuation maps for SPECT emission data, wherein the machine learning system includes a generator network 10 and a discriminator network 16. The artificial neural network is in the form of a deep convolutional neural network (CNN) and training of the deep CNN is described. In accordance with the present method and system, images reconstructed from photopeak window (126 keV-155 keV) 12$a$ (that is, the primary window) and scatter window (114 keV-126 keV) 12$b$ are concatenated as a multi-channel image and fed into a generator network 10, in particular, a deep neural network, to generate synthetic attenuation map) images. Specifically, a primary SPECT patch 12$a$' and a scatter SPECT patch 12$b$' are fed into the generator network 10 so as to maintain consistency with the voxel of the ground-truth attenuation map (ATTMAP) image patch 18' of the ground truth attenuation map (ATTMAP) image 18. While 126 keV-155 keV is used for photopeak window and 114 keV-126 keV is used for scatter window in the present work, other energy window number ranges could also produce satisfactory results. The generator network 10 with a GAN training strategy generates attenuation map images 14 from SPECT emission images, that is, the photopeak window (126 keV-155 keV) 12$a$ and scatter window (114 keV-126 keV) 12$b$ of the SPECT image. The GAN uses an additional discriminator network 16 to enforce the output of the generator network 10 to be consistent with the ground truth attenuation maps 18 (that is, attenuation maps generated based upon empirical evidence) as much as possible. An image gradient difference term is also added to the loss function to retain the sharpness of the generated attenuation maps.

While GAN is used as the overall training strategy and 3D U-net is used as the convolutional neural network of the generator network 10 in accordance with the disclosed invention, other network structures could also work. While both photopeak photons and scatter photons are disclosed herein as being used in accordance with the present invention, it is contemplated the concepts underlying the present invention may be applied using only photopeak photons or scatter photons in the production of attenuation maps for SPECT.

More particularly, and considering a specific embodiment of the present invention, SPECT patch images 12$a$', 12$b$' reconstructed from photopeak window (126 keV-155 keV) 12$a$ and scatter window (114 keV-126 keV) 12$b$ are concatenated as a multi-channel image and fed into the generator network 10, which, in accordance with a preferred embodiment, is 3D U-net deep convolutional neural network (CNN). As those skilled in the art will appreciate, 3D U-net deep convolutional neural networks (CNN) are well known deep neural networks.

The generator network 10 generates synthetic attenuation map (ATTMAP) image patches 14' intended to fool the discriminator that has been provided with a ground truth attenuation map image patch 18'. In accordance with this embodiment, the discriminator network 16 is a 3D convolutional neural network (CNN). As those skilled in the art will appreciate, 3D CNNs are well known deep neural networks used for image processing wherein every image input is treated as a matrix of voxel values which represents the brightness (amount of radiotracer concentration for SPECT) at a given voxel in the image such that CNNs extract information from voxels and the neighbors for various imaging tasks.

As discussed above, once the generator network 10 is fully trained it may be used without the discriminator network 16 to create attenuation map images 14.

I. Exemplary Embodiment

A specific implementation is described below. The implementation described below is a compilation of the initial results present in U.S. Provisional Application Ser. No. 62/836,167, entitled "METHOD AND SYSTEM FOR GENERATING ATTENUATION MAP FROM SPECT EMISSION DATA," filed Apr. 19, 2019, to which priority is claimed and which is incorporated herein by reference, and work performed after the filing of the '167 provisional application.

A conditional generative adversarial network (cGAN) framework is employed [Isola, P., Zhu, J.-Y., Zhou, T., Efros, A. A.: Image-to-image translation with conditional adversarial networks. In: Proceedings of the IEEE conference on computer vision and pattern recognition, pp. 1125-1134, (2017), which is incorporated herein by reference]. Referring to FIG. 1, two networks were simultaneously trained in the cGAN framework: a discriminator network D (designated as "16" in FIG. 1) that attempts to correctly discriminate between synthetic and real CT-based attenuation maps (that is, ground truth attenuation maps as discussed above), and a generator network G (designated as "10" in FIG. 1) that attempts to produce synthetic attenuation maps that will confuse the discriminator network D. To achieve this behavior, the generator loss $L_G$ and the discriminator loss $L_D$ are defined as:

$$L_G(X, Y) = L_{L2}(G(X), Y) + \lambda_1 L_{GDL}(G(X), Y) + \lambda_2 L_{ADV}(X) \quad (1)$$

$$L_D(X, Y) = \frac{1}{2}((D(Y) - T_{real})^2 + (D(G(X)) - T_{synthetic})^2) \quad (2)$$

where Y is the target CT-based attenuation maps, and G(X) is the generated attenuation map from the source SPECT image X by the generator network G. $L_{L2}$ is the L2 loss term. $L_{GDL}$ is the image gradient difference loss to address the inherent blurring caused by the L2 loss function, and is defined as:

$$L_{GDL}(A, B) = \||\nabla A_x| - |\nabla B_x|\|^2 + \||\nabla A_y| - |\nabla B_y|\|^2 + \||\nabla A_z| - |\nabla B_z|\|^2 \quad (3)$$

where $\nabla$ is the image gradient operator. [Nie, D., Trullo, R., Lian, J., Wang, L., et al.: Medical image synthesis with deep convolutional adversarial networks, IEEE Transactions on Biomedical Engineering 65, 2720-2730 (2018), which is incorporated herein by reference]. The adversarial loss terms are defined as the least square errors instead of binary cross entropy (BCE) since the least square GAN (LSGAN) was shown to be more stable when training than a regular GAN with BCE [Mao, X., Li, Q., Xie, H., Lau, R. Y., et al.: Least squares generative adversarial networks, In: Proceedings of the IEEE International Conference on Computer Vision, pp. 2794-2802, (2017), which is incorporated herein by reference]. $T_{real}=1$ and $T_{synthetic}=0$ are labels for the real and synthetic images, respectively. The adversarial loss term for the generator is defined as:

$$L_{ADV}(X) = \frac{1}{2}(D(G(X)) - T_{real})^2. \quad (4)$$

In Eq. (1), $\lambda_1$ and $\lambda_2$ are the weights for the $L_{GDL}$ and $L_{ADV}$ terms, respectively.

A. Network Architectures

Figure 2:
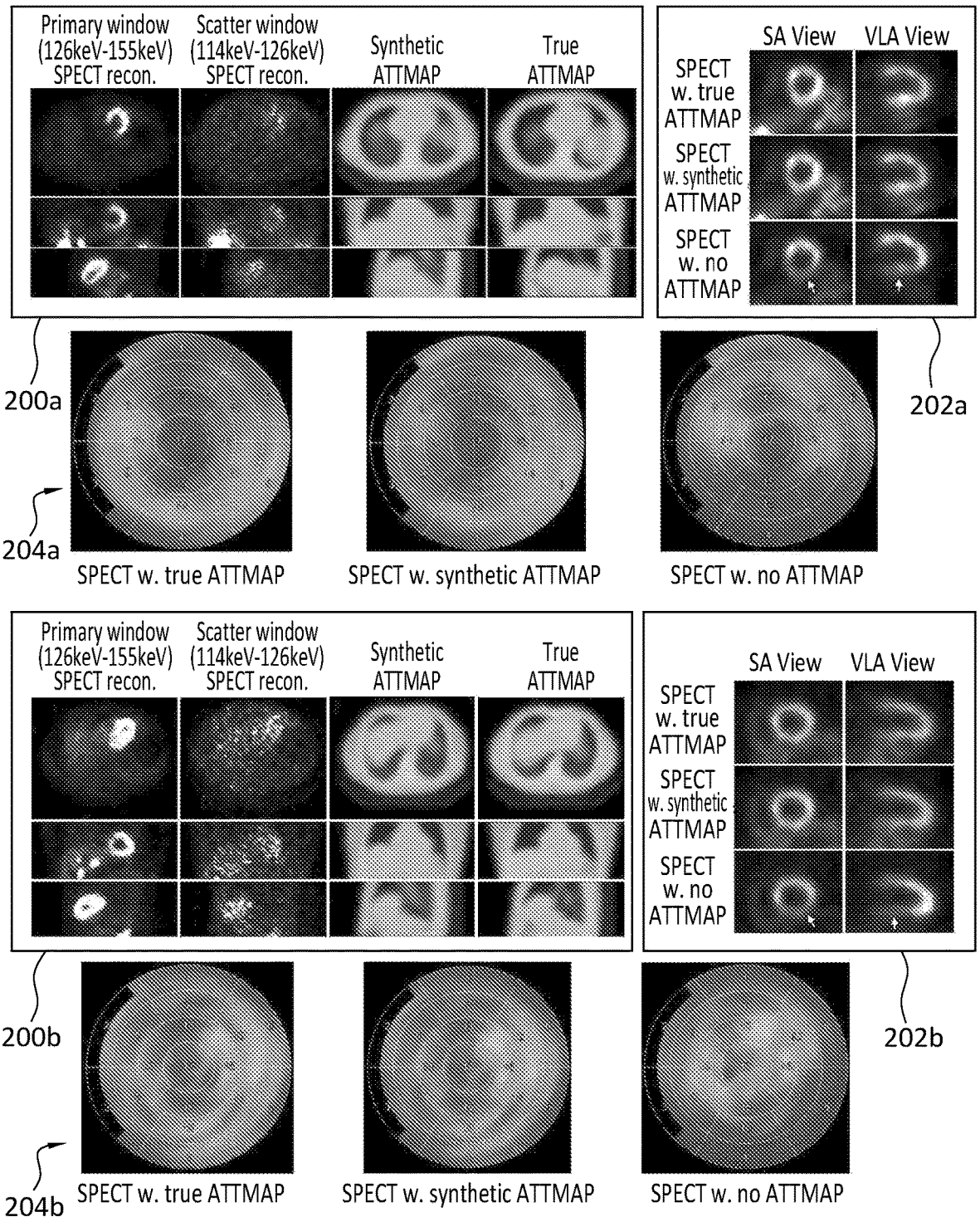
FIG. 2 shows results for two patients, wherein the upper left images show the primary/scatter window SPECT reconstructions, the synthetic attenuation maps, and CT (computer tomography)-based attenuation maps in the axial, coronal and sagittal views; the upper right images show SPECT reconstructed images corrected using CT-based attenuation maps, with synthetic attenuation maps generated by the Generative Adversarial Network (GAN) method using both primary and scatter windows data (AC-SPECT w. GAN-PS) and without attenuation correction in both short axis (SA) and vertical long axis (VLA) views; and the bottom images show the polar map comparisons.

A modified 3D version of the fully-convolutional U-net architecture is used as the generator network G (designated as "10" in FIG. 1) in accordance with the disclosed embodiment [Ronneberger, O., Fischer, P., Brox, T.: U-net: Convolutional networks for biomedical image segmentation, In: International Conference on Medical image computing and computer-assisted intervention, pp. 234-241, Springer, (2015), which is incorporated herein by reference]. U-net structure was selected for the purposes of the present image generation task, because both the input and the output are in the same image domain, and they share a lot of structure similarities, as can be seen in FIG. 1 and FIG. 2. There is also a great deal of low-level information shared between the input and output, and the U-net structure is desirable for its ability to shuttle this information directly across the net. A comparison between the U-net used and a fully convolutional network (FCN) can be found in Online Resource 1, where Applicant demonstrated the superior performance of U-net [Shi, L., Onofrey, J. A., Liu, H. et al. Deep learning-based attenuation map generation for myocardial perfusion SPECT. Eur J Nucl Med Mol Imaging (2020). https://doi.org/10.1007/s00259-020-04746-6, which is incorporated herein by reference, wherein the online resource can be found at the bottom 'Electronic supplementary material' at https://link.springer.com/article/10.1007/s00259-020-04746-6 and is substantially reproduced below with reference to the discussion regarding FIG. 8 and Table 4].

The modified U-net architecture is used as the generator network G in accordance with the disclosed embodiment is four levels deep, which is one level fewer than the original U-net. The disclosed embodiment uses one level fewer than the standard U-net because of the much smaller image patch size of 16×16×16 (because of the limited resolution and relatively large voxel size in SPECT) used in accordance with the disclosed embodiment instead of the commonly used 32×32×32 or even larger image patch sizes. This was a necessary design decision due to the dimensions of the image patches used for training on limited GPU resources. As those skilled in the art will appreciate, the number of levels in the U-net may vary depending upon other factors. Symmetric padding was applied prior to each convolution operation to account for reduced image (or feature map) sizes due to applying the convolution filters. This allows the network's output layer to have the same size as the input layer [Milletari, F., Navab, N., Ahmadi, S.-A.: V-net: Fully convolutional neural networks for volumetric medical image segmentation, In: 2016 Fourth International Conference on 3D Vision (3DV), pp. 565-571, IEEE, (2016), which is incorporated herein by reference]. Batch normalization (BN) was applied after each convolutional layer and before the ReLU (rectified linear unit). Dropout with a rate of 0.15 was applied to the bottleneck layer of the U-net in the training phase to prevent overfitting, but is removed during testing.

The discriminator network D (of the discriminator network 16) is a typical CNN architecture that includes three stages of convolution, BN, ReLU, and max pooling, followed by three fully connected layers. The filter size is 3×3×3, the number of the filters is 32, 64, 128 for the convolutional layers, and the number of the output nodes in the fully connected layers is 512, 128, and 1. The overall illustration of the proposed method and the networks used are shown in FIG. 1.

B. Multi-Channel SPECT Inputs

As mentioned above, both photopeak photons and scatter photons contain information that helps estimate the attenuation distribution [Pan, T.-S., King, M. A., Luo, D.-S., Dahlberg, S. T., et al.: Estimation of attenuation maps from scatter and photopeak window single photon-emission computed tomographic images of technetium 99m-labeled sestamibi, Journal of Nuclear Cardiology 4, 42-51 (1997), which is incorporated herein by reference]. The photopeak window images 12a are expected to provide more information on the inner organs including lung, heart, and liver, whereas the scatter window images 12b are expected to provide more accurate patient body boundaries. In accordance with the present invention, and as discussed above, SPECT patch images 12a', 12b' reconstructed from photopeak window (126 keV-155 keV) and scatter window (114 keV-126 keV) are concatenated as a multi-channel image and fed into the deep neural networks of the generator network 10 to generate synthetic attenuation maps.

C. Image Preprocessing

The patient bed was manually cropped from the label CT-attenuation maps since the bed information is not available in the SPECT images. For fair comparison, the bed was later put back into the predicted attenuation maps before applying attenuation correction. In clinical applications, the bed position is always known, and the bed attenuation can be recovered using a pre-scanned and stored template.

Image normalization is a key pre-processing step for deep learning algorithms [Onofrey, J. A., Casetti-Dinescu, D. I., Lauritzen, A. D., Sarkar, S., et al.: Generalizable Multi-site Training and Testing of Deep Neural Networks Using Image Normalization, In: Biomedical Imaging (ISBI), 2019 IEEE 16th International Symposium on, pp. 348-351 (2019), which is incorporated herein by reference]. Unlike transmission CT images in which image intensity in terms of Hounsfield Unit (HU) represents the tissue attenuation and are consistent among patients, the SPECT image intensity represents the tracer activity and thus varies among patients due to multiple factors, including different tracer injection dose, time delay from injection to imaging, isotope decay, patient weight, etc. Image normalization is critical when applying deep learning algorithms on nuclear images. Two common normalization methods include maximum-normalization (which normalizes the image intensities by the maximum intensity to have values within the range [0,1]) and Gaussian-normalization (which shifts and scales the image intensity to have zero mean and variance). However, the two common methods are either sensitive to noise-induced variances or rely on the assumption of the intensities being Gaussian, which is not always true. In accordance with a preferred embodiment, a mean-normalization approach is used that normalizes each channel of the SPECT images by the mean intensity of the entire 2-channel SPECT image volume, which serves as an indicator of the average activity. As will be discussed later, this approach provided more stable results.

D. Network Training Parameters

In this disclosed embodiment, the network training parameters were selected based on pilot dataset testing. In training, 3D image patches 12a', 12b', 18' with a size of 16×16×16 voxels were used since both SPECT images 12a, 12b and ground-truth attenuation maps 18 have the same voxel size of 6.8×6.8×6.8 mm³. The generator network 10 and discriminator network 16 were trained with the Adam optimizer, which is an adaptive learning rate optimization algorithm designed for training deep neural networks [Diederik P. Kingma and Jimmy Lei Ba. Adam: A method for stochastic optimization. 2014. arXiv:1412.6980v9, which is incorporated herein by reference]. An initial learning rate of $10^{-3}$ was used for training the generator network 10 and $5 \times 10^{-4}$ was used for training the discriminator network 16. Both learning rates were decayed by a factor of 0.99 after each epoch. The generator network 10 was trained using $\lambda_1=1$ and $\lambda_2=20$. The generator network 10 and discriminator network 16 were trained for 400 epochs. In each epoch, 12,800 patches were randomly sampled from the training data and the batch size was set to 16. In the testing phase, the entire 3D image was fed into the trained the generator network 10 and discriminator network 16 to avoid stitching artifacts. The framework was implemented using TensorFlow [Abadi M, Barham P, Chen J, Chen Z, Davis A, Dean J, et al. Tensorflow: A system for large-scale machine learning. $12^{th}$ Symposium on Operating Systems Design and Implementation ({OSDI} 16); 2016. p. 265-83, which is incorporated herein by reference]. The training phase takes about 10 hours on an NVIDIA GTX 1080 Ti GPU. In the testing phase, it takes less than 1 second to generate an attenuation map from SPECT data. It should be appreciated that for testing, the whole image was used (not 32×32×32 patches) as such functionality is allowed by the U-net architecture.

E. Initial Evaluation

Initially, 40 subjects were included in the training set, and 25 subjects were used for evaluation. To evaluate the proposed mean-normalization approach, the cGAN was trained with data pre-processed with mean-normalization, Gaussian-normalization, and maximum-normalization. The predicted attenuation maps were then compared with the CT-attenuation maps in terms of normalized mean absolute error (NMAE) and mean squared error (MSE), where NMAE is defined as: $NMAE=(\Sigma_{x,y,z}|P(x,y,z)-Q(x, y, z)|)/(N \cdot (MAX_I-MIN_I))$, where P and Q represent the predicted and the reference CT-based attenuation maps, $MAX_I$ and $MN_I$ are the maximum and minimum intensities of the reference image, respectively, and N is the total number of voxels.

The results of cGAN were compared using both primary and scatter inputs (GAN-PS), using primary inputs alone (GAN-P), and using scatter inputs alone (GAN-S). The comparisons using different inputs were also repeated with U-net without the adversarial training strategy (UNET-PS, UNET-P and UNET-S). NMAE and MSE were used to evaluate the predicted attenuation images. The predicted attenuation maps were further applied for attenuation correction on the SPECT images, and the attenuation corrected SPECT (AC-SPECT) using the predicted attenuation maps ($AC_p$) were evaluated against the AC-SPECT images corrected with CT-attenuation maps ($AC_{CT}$) using NMAE and regional ROI percentage bias, where the ROIs were manually drawn on the myocardium ($Bias_{myo}$) and blood pool ($Bias_{blp}$) for each testing subject. The ROI bias was calculated as $100\% \times (\Sigma_{i \in ROI}AC_p(i) - \Sigma_{i \in ROI}AC_{CT}(i))/\Sigma_{i \in ROI}AC_{CT}(i)$. Paired t-test was also performed to determine if the ROI biases are significantly different from zeros.

F. Complete Evaluation

Thereafter, 65 consecutive clinical subjects (including the 40 subjects from the initial evaluation) with both normal and abnormal patients were scanned at Yale New Haven Hospital with $^{99m}Tc$-tetrofosmin for myocardial perfusion SPECT studies. One day stress-only low-dose protocol, with the mean administered dose of 15 mCi, was used. The clinical characteristics of the patients enrolled in the study, including gender, age, height, weight and body mass index (BMI), are given in Table 1. Both SPECT and attenuation CT images were acquired on a GE NM/CT 850 SPECT/CT scanner. The SPECT data were acquired using 60 angles covering a 180-degree orbit. Both the photopeak window (126.5 keV-154.5 keV) and scatter window (114 keV-126 keV) SPECT projection data were acquired and reconstructed using ordered-subset maximization expectation algorithm (OSEM), 5 iterations and 6 subsets [Hudson H M, Larkin R S. Accelerated image reconstruction using ordered subsets of projection data. IEEE transactions on medical imaging. 1994; 13:601-9, which is incorporated herein by reference]. The attenuation CT data were acquired right after the SPECT scans with 120 kVp and 20 mAs and then converted to attenuation maps corresponding to 140 keV with a voxel size of 6.8×6.8×6.8 mm$^3$ using the scanner software. The attenuation maps were in the unit of cm$^{-1}$. The CT-based attenuation maps were manually registered with the SPECT images using the scanner software if there was any mismatch. The size of the SPECT reconstruction images is 64×64×64, though the attenuation maps typically have a shorter scanning range in the axial direction (25-35 slices) to reduce unnecessary radiation, therefore the SPECT images were cropped in the longitudinal direction to match the attenuation maps accordingly for each patient.

TABLE 1

The gender, age, height, weight, and BMI distribution of the enrolled patients.

| | | Age (year) | Height (cm) | Weight (kg) | BMI |
|---|---|---|---|---|---|
| Training Data | Range | 31-95 | 147-185 | 41.7-104.5 | 13.9-35.5 |
| (19 M, 21 F) | Mean ± Std. | 66.1 ± 13.0 | 166.7 ± 10.3 | 72.6 ± 14.4 | 26.1 ± 4.4 |
| Testing Data | Range | 39-88 | 148-193 | 48.4-115.8 | 19.3-34.6 |
| (15 M, 10 F) | Mean ± Std. | 65.5 ± 13.4 | 171.6 ± 12.0 | 74.0 ± 15.5 | 25.0 ± 3.5 |

M stands for male and F stands for female.

Results

F.1. Impact of Image Normalization

Table 2 shows the mean, standard deviation (STD) and interquartile range (IQR) of the NMAE and MSE between the predicted attenuation maps using GAN-PS and the CT-based attenuation maps for the three normalization methods. Though the mean NMAE and MSE are similar for the three methods, the mean normalization (Mean-Norm) obtained substantially lower STD and IQR compared with the other two methods, suggesting that mean normalization is more robust in this nuclear imaging application. Thus, only mean normalization was used in the following studies.

TABLE 2

The mean, STD and IQR of the NMAE and MSE between predicted attenuation maps using GAN-PS and the CT-attenuation maps for the three normalization methods.

| | Mean-Norm | | Gaussian-Norm | | Max-Norm | |
|---|---|---|---|---|---|---|
| Metric | % NMAE | MSE | % NMAE | MSE | % NMAE | MSE |
| Mean | 3.60 | 189 | 3.56 | 215 | 3.78 | 229 |
| STD | 0.83 | 87.2 | 1.60 | 229 | 1.62 | 254 |
| IQR | 0.95 | 66.2 | 1.21 | 97.2 | 0.98 | 95.4 |

F.2. Effectiveness

FIG. 2 shows two sample studies. In each study, the upper left images (200a, 200b) are the primary window and the scatter window SPECT images used as inputs as well as the synthetic attenuation map (ATTMAP) generated by the cGAN model (GAN-PS) in accordance with the present invention. Employing the methodology of the present invention, consistent synthetic attenuation maps were generated with the ground-truth CT-based attenuation maps. The upper right images (202a, 202b) in FIG. 2 for each subject show that the SPECT reconstructed images corrected using the CT-based attenuation map and the synthetic attenuation map (GAN-PS) are nearly identical, whereas obvious attenuation artifacts can be observed in the non-attenuation corrected images, as pointed by the arrows. The 17-segment polar maps 204a, 204b for each subject in FIG. 2 (generated using Carimas software package) of the SPECT images corrected by both synthetic and CT-based attenuation maps are also consistent. In contrast, the polar maps without attenuation correction clearly show different patterns.

F.3. Impact of Multi-Channel Inputs and GAN

Figure 3:
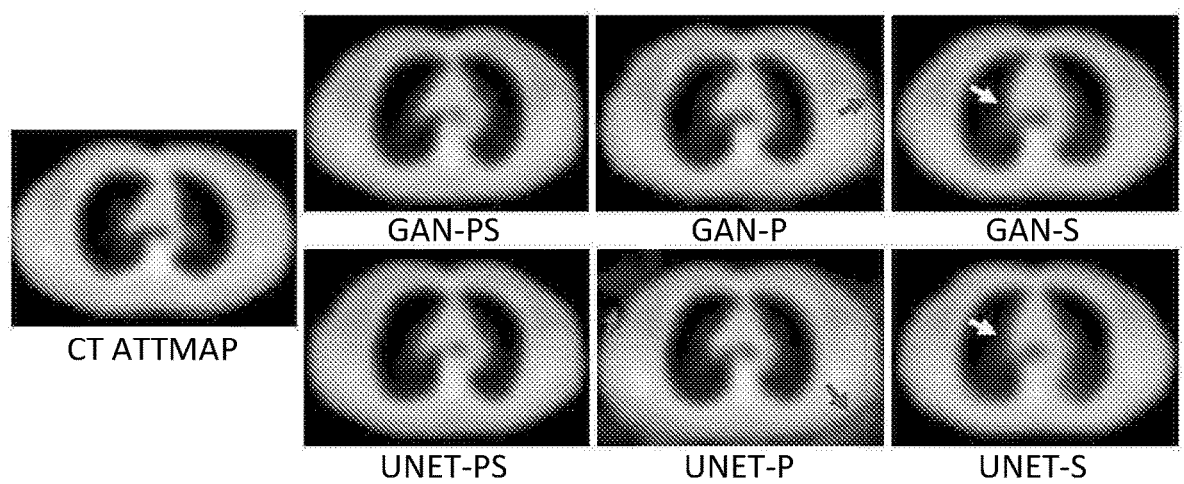
FIG. 3 shows visual comparison of GAN and U-net using different inputs: both primary and scatter windows (PS), primary window alone (P), and scatter window alone (S).

Referring to FIG. 3, it can be observed that for both GAN and U-net methods, using both the primary and scatter channels as inputs produced results closer to the ground truth CT attenuation map. Inaccurate body boundary recovery and artifacts (dark arrows) were observed in GAN-P and UNET-P's results, and incorrect inner organ shape was observed (white arrows) in the results from GAN-S and UNET-S. This was expected since the primary window alone cannot provide sufficient body boundary information, whereas the scatter window alone can only provide weak inner organ boundary information, as can be seen in FIG. 2. Interestingly, when using only the primary window as input, GAN obtained much better result than U-net, where severe artifacts were observed near the body boundary area in the UNET-P result. This suggests that GAN training is able to obtain more stable results when limited information is available.

Figure 4:
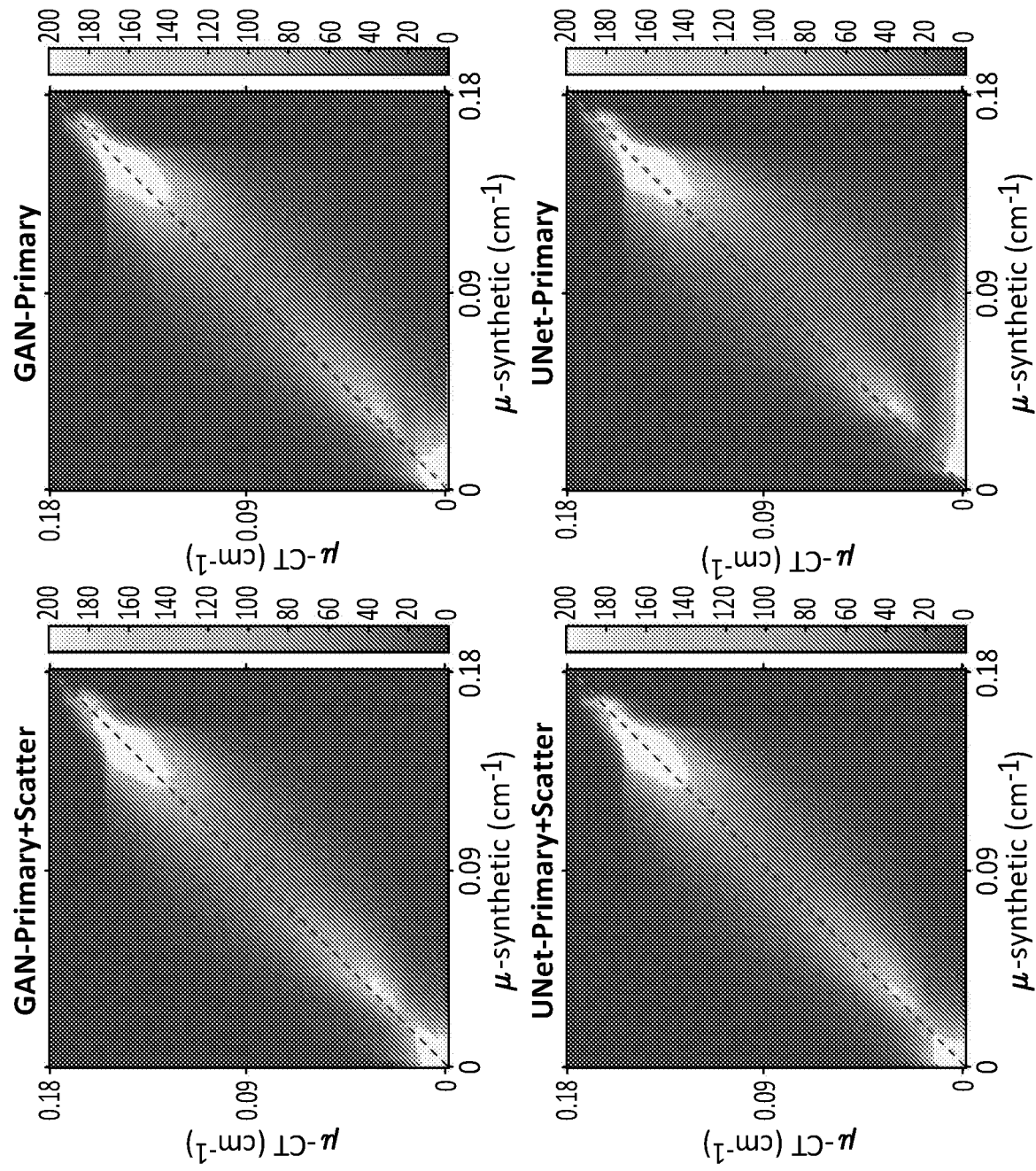
FIG. 4 shows correlation between the attenuation coefficient of synthetic attenuation map ($\mu$-Synthetic) and CT-based attenuation map ($\mu$-CT) for all the voxels in the 25 testing human subjects using various combinations of deep learning models (GAN vs. U-net) and input data (Primary+Scatter vs. Primary only). Dashed lines are the identity lines.
Figure 5:
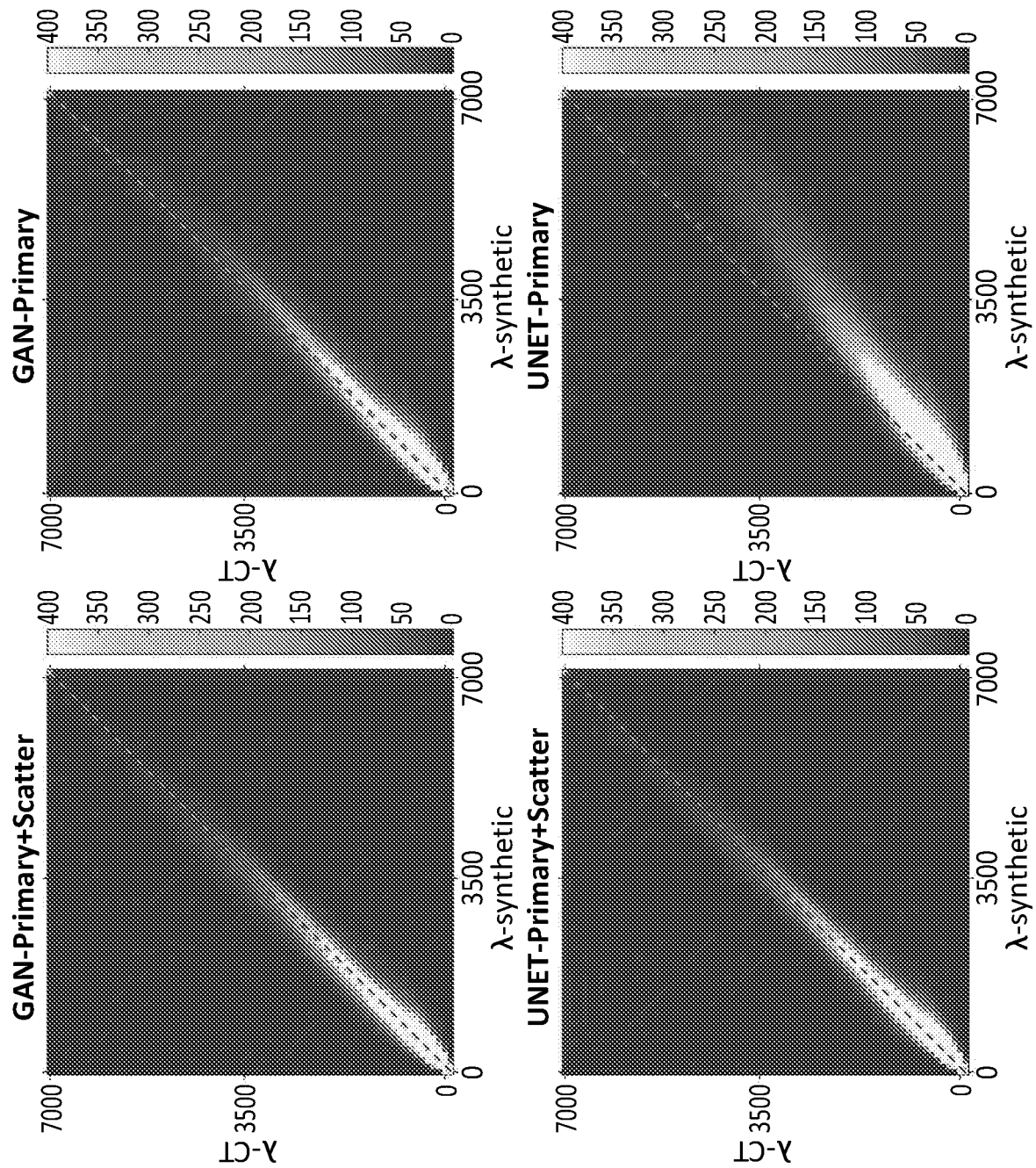
FIG. 5 shows correlation between attenuation-corrected SPECT reconstructed images using synthetic attenuation map ($\lambda$-Synthetic) and CT-based attenuation map ($\lambda$-CT) for all the voxels in the 25 testing human subjects using various combinations of deep learning models (GAN vs. U-net) and input data (Primary+Scatter vs. Primary only). Dashed lines are the identity lines.

The numerical results in Table 3 are consistent with the visual inspection. Due to the substantial artifacts around the body boundary, UNET-P produced the worst results regarding attenuation map estimation and attenuation correction, among all the methods. In comparison, the GAN counterpart (GAN-P) produced more stable results. The GAN-PS, GAN-S, UNET-PS, and UNET-S methods surprisingly obtained similar NMAE and MSE on the generated attenuation maps (p) and attenuation corrected SPECT images (A). FIG. 4 shows the correlation between the synthetic attenuation maps (p-Synthetic) using GAN-PS, GAN-P, UNET-PS, and UNET-P methods, and the CT-based attenuation maps (p-CT) for all the voxels in the 25 testing subjects. Similarly, FIG. 5 shows the corresponding correlation between the attenuation-corrected SPECT images for all the voxels in the 25 testing subjects. From FIG. 4 and FIG. 5 it can be observed that when both primary and scatter windows were used, both GAN-PS and UNET-PS obtained accurate results. However, when only primary windows are used, GAN-P clearly outperformed UNET-P and obtained very similar results as GAN-PS and UNET-PS.

Figure 6:
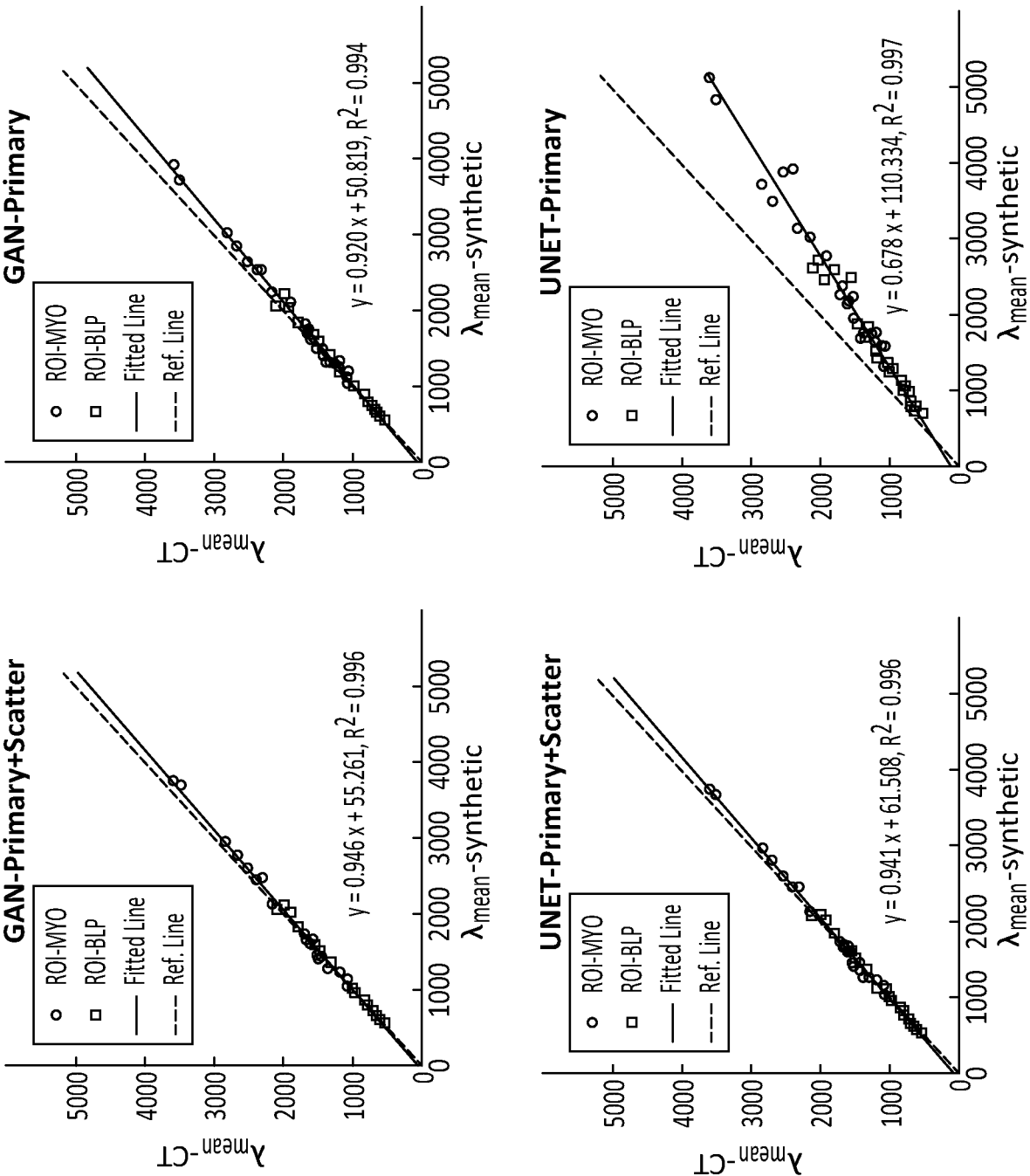
FIG. 6 shows scatter plots of region of interest (ROI) mean voxel values measured on left ventricle myocardium (MYO) and blood pool (BLP) between the attenuation-corrected SPECT reconstructed images using synthetic attenuation map ($\lambda$ mean-Synthetic) and CT-based attenuation map ($\lambda$ mean-CT) for all the voxels in the 25 testing human subjects using various combinations of deep learning models (GAN vs. U-net) and input data (Primary+Scatter vs. Primary only).
Figure 7:
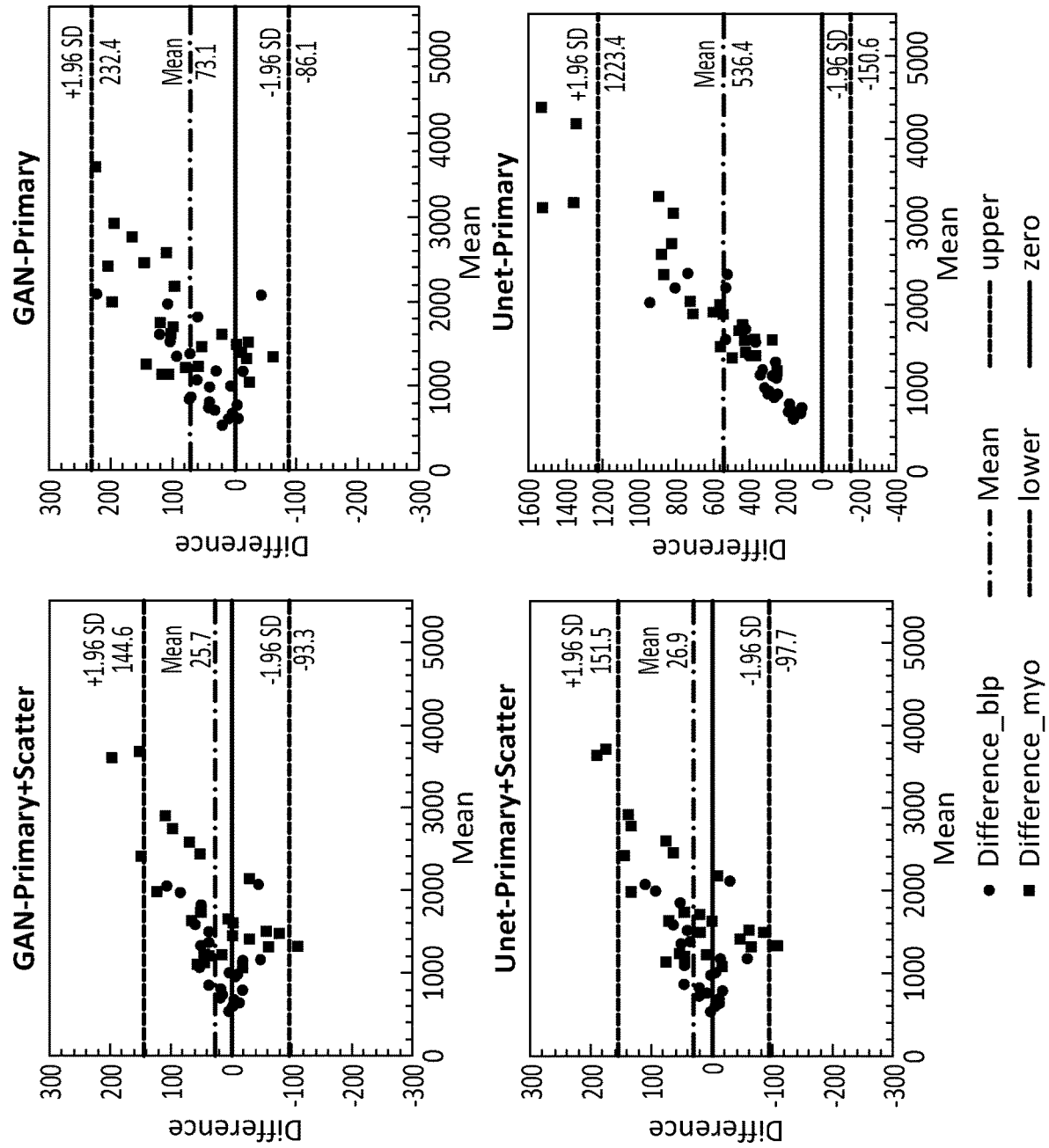
FIG. 7 shows Bland Altman plots of ROI mean voxel values measured on left ventricle myocardium (MYO) and blood pool (BLP) between the attenuation-corrected SPECT reconstructed images using synthetic attenuation map and CT-based attenuation map for all the voxels in the 25 testing human subjects using various combinations of deep learning models (GAN vs. U-net) and input data (Primary+Scatter vs. Primary only).

Nonetheless, the heart is the organ of interest in this evaluation, and the local ROI evaluation on myocardium (myo) and blood pool (blp) showed that the GAN-PS and UNET-PS achieved the lowest ROI bias among all the methods, which are found to be not significantly different (p-value>0.05) from the results with CT-based attenuation maps (Table 3) based on two-tailed Student's t-test. Note that for both GAN and U-net, the standard deviations of bias are much lower when both primary and scatter windows were used as input, compared with the results based only on primary window input. FIG. 6 and FIG. 7 show the scatter plots and Bland-Altman plots of the ROI mean value measurements between $\lambda$-Synthetic (GAN-PS, GAN-P, UNET-PS and UNET-P) and $\lambda$-CT. Similar to Applicant's previous observations, GAN-P performed slightly worse than GAN-PS and UNET-PS, but much better than UNET-P.

TABLE 3

Averages and STDs of the NMAE and PSNR of the predicted attenuation maps (NMAE-$\mu$, MSE-$\mu$), the NMAE of the AC-SPECT (NMAE-$\lambda$) and the regional percentage bias of the AC-SPECT on myocardium and blood pool (Bias$_{myo}$ and Bias$_{blp}$) by different methods.

| Metric | GAN-PS | GAN-P | GAN-S | UNET-PS | UNET-P | UNET-S |
|---|---|---|---|---|---|---|
| % NMAE-$\mu$ | 3.60 ± 0.85 | 5.12 ± 1.03 | 3.62 ± 0.86 | 3.60 ± 0.85 | 24.3 ± 1.76 | 3.65 ± 0.82 |
| MSE-$\mu$ | 189 ± 89 | 270 ± 123 | 192 ± 94 | 185 ± 92 | 2594 ± 207 | 190 ± 89 |
| % NMAE-$\lambda$ | 0.26 ± 0.15 | 0.30 ± 0.17 | 0.27 ± 0.16 | 0.26 ± 0.15 | 0.92 ± 0.48 | 0.27 ± 0.16 |
| % Bias$_{myo}$ | 3.48 ± 2.05 | 5.75 ± 3.39 | 4.36 ± 2.54 | 3.81 ± 2.13 | 37.9 ± 9.84 | 3.67 ± 2.45 |
| % Bias$_{blp}$ | 2.43 ± 1.42 | 4.34 ± 3.04 | 2.69 ± 2.06 | 2.49 ± 1.52 | 31.5 ± 9.08 | 2.46 ± 1.86 |

F. 4. Impact of BMI and Gender 25 testing subjects were further divided the into lean (BMI<=25) and overweight (BMI>25) groups, as well as male and female groups. This resulted in 15 male subjects and 10 female subjects, and 12 lean subjects (7/15 male, 5/10 female) and 13 overweight subjects (8/15 male, 5/10 female). Unpaired t-test (with equal variance) on the measured biases on the AC-corrected SPECT images did not show significant differences between lean and overweight subjects (p=0.824 on LV myocardium ROI and p=0.408 on LV blood-pool ROI). The mean biases for both myocardium and blood pool are very small for either lean (<1.5%) or overweight (<1%) subjects. None of them was significant from zeros according to paired t-test. Between male and female subjects, unpaired t-test also did not show significant differences (p=0.152 on LV myocardium ROI and p=0.075 on LV blood-pool ROI), although the female group showed higher mean bias (<2.6%) than the male group (<0.3%). The biases for the female group are also found to be significantly different from zeros (p=0.036 on LV myocardium ROI and p=0.044 on LV blood-pool ROI), whereas the biases for the male group are not significant from zeros.

G. Alternate Evaluation

In accordance with another example, a training set of 40 human subjects with both cardiac SPECT with $^{99m}$Tc-tetrofosmin and attenuation CT scans, and a testing set of 8 subjects not involved in the network training were employed using the Generative Adversarial Network (GAN) training strategy described above. The SPECT and CT images were acquired from a GE NM/CT 850 SPECT/CT scanner.

The network structures and parameters were as follows:
Generator: U-net 3D
Discriminator: CNN 3D
Patch size: 16×16×16 (6.797 mm×6.797 mm×6.797 mm)
Epoch size: 12800
Batch size: 16
Number of epochs: 400
Adversarial loss: Adversarial_Least_Squares
Main loss: L2
Gradient loss weight: 1.0

The synthetic attenuation maps generated by the generator network 10 were compared with the true attenuation maps by the discriminator network 16 regarding both global Normalized Mean Absolute Error (NMAE=MAE(synthetic)/[max(true)−min(true)]) and localized region of interest (ROI) absolute percentage error (|(roi_mean(synthetic)−roi_mean(true))/roi_mean(true)|) in left ventricle (LV) myocardium (121.8±30.0 cm$^3$) and LV blood pool (40.7±7.5 cm$^3$) ROIs. The localized absolute percentage error was also calculated for attenuation corrected SPECT reconstruction images with both true and synthetic attenuation maps.

G.1. Comparison of U-Net with FCN

Figure 8:
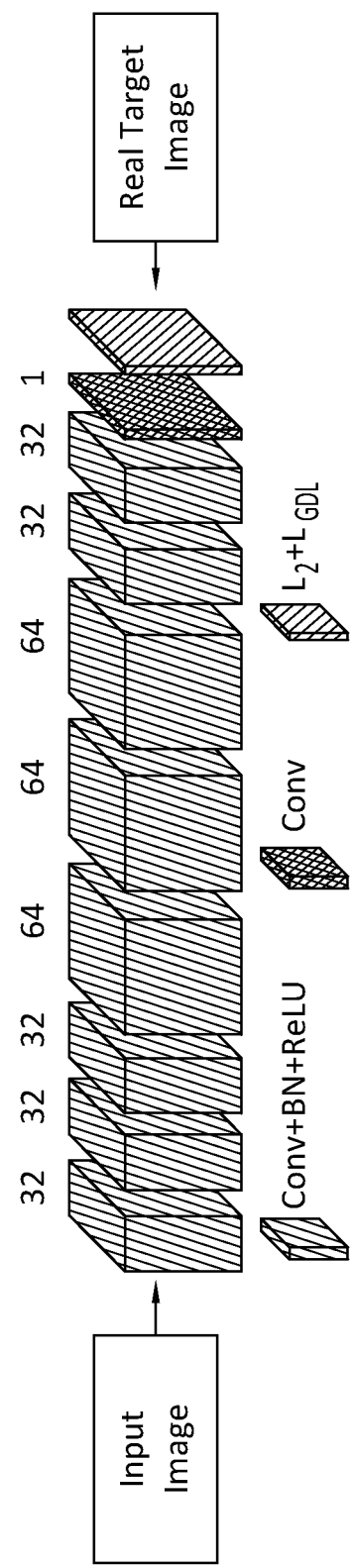
FIG. 8 is a schematic of the fully convolutional network (FCN) structure used for comparison purposes with disclosed embodiments.

Additional experiments were performed to compare the U-net structure of the present invention with a fully convolutional network (FCN) as the generator network when using GAN in a manner similar to the FCN structure used by Nie et al. [Nie D, Trullo R, Lian J, Wang L, Petitjean C, Ruan S, et al. Medical image synthesis with deep convolutional adversarial networks. IEEE Transactions on Biomedical Engineering. 2018; 65:2720-30, which is incorporated herein by reference]. An FCN network with 9 layers containing convolution, batch normalization (BN), and ReLU operations was developed. The numbers of filters are 32, 32, 32, 64, 64, 64, 32, 32, and 1, respectively, for the individual layers. The kernel sizes are 3×3×3 for the first 8 layers and 1×1×1 for the last layer. The same kernel size settings as in Nie et al. were not used because they were using 32×32×32 input and 16×16×16 output image patches and thus needing several big kernels to keep the network from getting too deep, whereas in accordance with the present invention both the input and output image patch sizes are 16×16×16, so the kernel size of 3 was used for all the layers except for the last one in order to have a fair comparison with previous studies. This FCN network was used as the generator while keeping the other parameters the same and compared with using U-net as the generator. An illustration of the FCN network structure that was used in accordance with a disclosed embodiment is shown in FIG. 8. Briefly, the FCN network structure includes multiple blocks composed of a convolutional layer (Cony), batch normalization layer (BN), and ReLU layer (ReLU), a convolutional block, and a block accounting for image gradient difference loss to address the inherent blurring caused by the $L_2$ loss function. The comparison results are shown Table 4. As can be seen, U-net achieved superior results than FCN on every metric that we compared.

TABLE 4

Averages and STDs of the NMAE and MSE of the predicted attenuation maps (NMAE-$\mu$, MSE-$\mu$), the NMAE (NMAE-$\lambda$) of the reconstructed SPECT images with attenuation correction (AC-SPECT), and the regional percentage bias of the AC-SPECT on myocardium and blood pool ($Bias_{myo}$ and $Bias_{blp}$) by using U-net and FCN as the generators of GAN (both primary window and scatter window are used).

| Metric | GAN-PS-U-net | GAN-PS-FCN |
|---|---|---|
| % NMAE-$\mu$ | 3.60 ± 0.85 | 4.22 ± 0.94 |
| MSE-$\mu$(×10$^{-4}$) | 1.89 ± 0.89 | 2.30 ± 1.05 |
| % NMAE-$\lambda$ | 0.26 ± 0.15 | 0.31 ± 0.19 |
| % $Bias_{myo}$ | 1.33 ± 3.80† (p = 9.9 × 10$^{-2}$) | 1.54 ± 3.59 (p = 4.7 × 10$^{-2}$) |
| % $Bias_{blp}$ | 1.07 ± 2.58† (p = 5.3 × 10$^{-2}$) | 1.51 ± 2.76 (p = 1.3 × 10$^{-2}$) | p-values of the paired t-test results were also given for regional percentage bias.
†indicates that the results with synthetic attenuation maps showed no significant differences from the results with CT-based attenuation maps.
Bold font indicates the optimal performers for each error/bias metric.

As a result of this a Generative Adversarial Network (GAN) training strategy, the method of the present invention successfully generated accurate synthetic attenuation maps close to the true attenuation map, both qualitatively and quantitatively. The single photon emission computed tomography (SPECT) reconstructed images corrected using the true attenuation map and synthetic attenuation map are almost identical, whereas obvious attenuation artifacts can be observed in the non-attenuation corrected images. The global Normalized Mean Absolute Error (NMAE) of the synthetic attenuation maps across the testing subjects were 3.4%±1.1%, whereas the localized percentage error was 0.5%±0.4% in LV myocardium and 0.5%±0.2% in LV blood pool. The localized absolute percentage error calculated for attenuation corrected SPECT reconstruction images was 3.2%±1.5% in LV myocardium and 2.5%±1.3% in LV blood pool.

II. Offline Embodiment

The system described above for generating accurate attenuation maps from emission data typically requires that the systems described herein be incorporated into iterative image reconstruction software of SPECT vendors. In order to facilitate the wide use of the deep learning generated attenuation map described above without the need for incorporation of the systems described above into iterative image reconstruction software of SPECT vendors and so as to allow for use of the systems described above in a manner independent of SPECT vendor software, the following "offline" approach to perform attenuation correction based on NAC (non-attenuation corrected) SPECT images for parallel-hole SPECT scanners can be used.

The attenuation map (ATT MAP) used for attenuation correction can be either generated from NAC SPECT image dataset (photopeak window or both photopeak combined with scatter windows) using the deep learning method described above or acquired from transmission CT scanner. Where the attenuation map is acquired from transmission CT scanner, additional conversion from CT image to attenuation map and the registration between the SPECT image and attenuation map is required.

A. Associated Offline-Scanner Attenuation Correction

Figure 9:
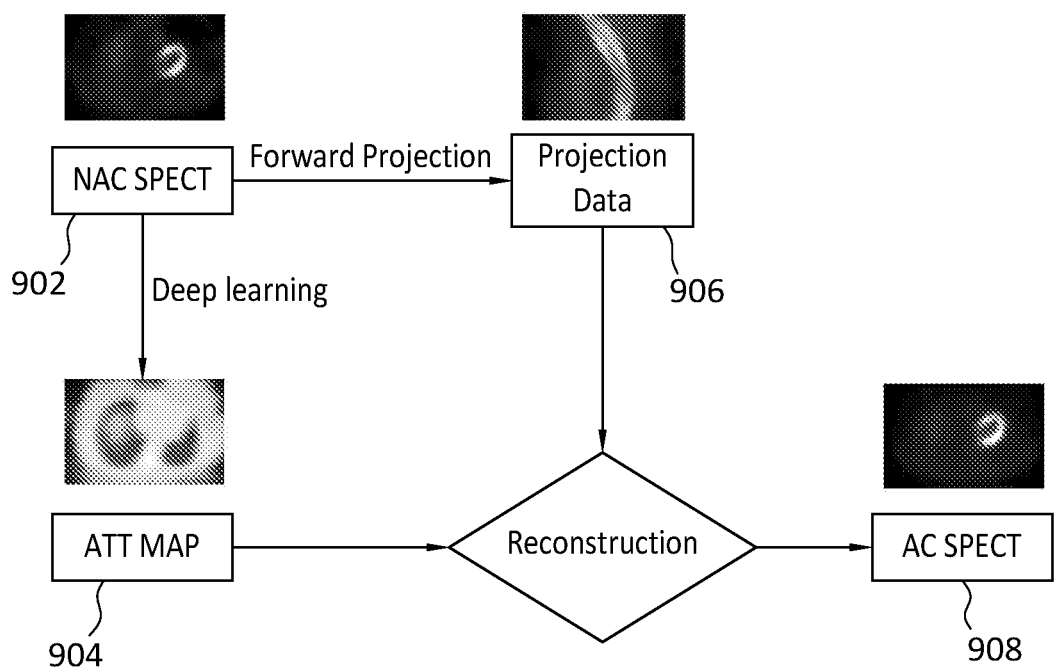
FIG. 9 shows the workflow of the offline scanner attenuation correction for NAC SPECT.

To utilize such deep learning-based approach described above for SPECT attenuation correction, the synthetic attenuation maps generated by deep learning approaches described in this invention typically need to be incorporated into iterative image reconstruction software of SPECT vendors. To facilitate the wide use of the deep learning generated attenuation map approach described in this invention independent of vendor software, Applicant describes an invention of an offline approach to perform attenuation correction based on NAC SPECT images without the need of accessing to vendor software. As shown in FIG. 9, the NAC SPECT image dataset 902 (photopeak window or both photopeak combined with scatter windows) is first used to generate the attenuation map 904 using the deep learning method described above (that is, for example, the well-trained network (10 in FIG. 1 described above) was used to estimate the attenuation map and there is therefore no need for a ground truth image). The NAC SPECT image dataset can be two images both from primary window and scatter window, or an image from one window. Attenuated projection data 906 is estimated at the same projection angle with those used in the scanning protocol via forward projecting the NAC SPECT image in the primary window without the attenuation map. Here, since the SPECT scanner typically used the scanning protocol to acquire the projection with a 180° orbit, right anterior oblique (RAO) to left posterior oblique (LPO) for cardiac studies, it was possible to also estimate the projection across 180° from RAO to LPO. Such forward projection can be performed on a virtual geometry and is not limited to the above described 180° acquisition, but can also include 360° acquisition or other acquisitions, both without and with body contour information. Then the AC SPECT image 908 is reconstructed from the estimated attenuated projection data 906 using iterative reconstruction (e.g. OSEM) with attenuation correction using the attenuation map 904 generated by the deep learning approach described above. The iterative number and subset configuration is typically the same with that used in reconstructing the NAC image, such as 5 iterations and 6 subsets in this evaluation, but can also vary to optimize the convergence [Hudson H M, Larkin R S. Accelerated image reconstruction using ordered subsets of projection data. Medical Imaging, IEEE Transactions on Medical Imaging, 1994, 13(4): 601-609), which is incorporated herein by reference].

Figure 10:
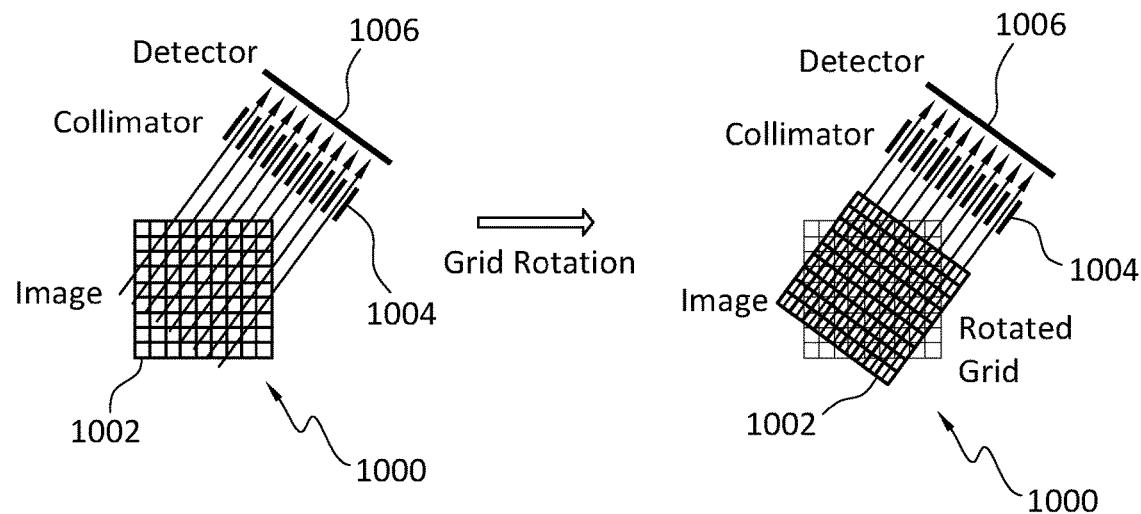
FIG. 10 is a schematic of a rotation-based projector for use in accordance with an embodiment of the present invention.

In accordance with one embodiment, the same system matrix is used in the forward projection and image reconstruction, which is calculated using the image rotation-based projector 1000 as shown in FIG. 10. For each rotation angle, the image grids 1002 are rotated first to make sure the rotated grids are parallel to the collimator holes 1004. Then the forward projection toward the detector 1006 and back projection into image space are calculated based on the image grids 1002 using established calculation techniques [see, for example, the section 4.1 "rotation projector" in Zeng, G. L., and G. T. Gullberg. "Frequency domain implementation of the three-dimensional geometric point response correction in SPECT imaging." *IEEE transactions* on *Nuclear Science* 39.5 (1992): 1444-1453, which is incorporated herein by reference]. Although the rotation-based forward-projector/back-projector is used in this implementation and evaluation, other forward-projector/back-projector methods, such as ray-tracing methods, can all be applied.

While one embodiment is disclosed above to implement attenuation correction given an attenuation map, it is appreciated other techniques may be implemented within the spirit of the present invention.

Using the previously described technique, Applicant demonstrated this approach initially using two human datasets (one female and one male, age: 56 and 71 years old, weight: 88.0 and 86.2 kg, BMI:27.8 and 27.2 kg/m$^2$) who underwent the MPI stress studies on GE NM/CT 850 SPECT/CT scanner at Yale New Haven hospital. Routine step and shoot L mode protocol was used to acquire the emission projection data at 60 angles over 180 degrees. On the scanner, the photopeak window (126.5 keV-154.5 keV) projection data were used to reconstruct the NAC SPECT image with ordered-subset maximization expectation algorithm (OSEM, 5 iterations and 6 subsets). The size of the SPECT reconstruction images is 64×64×64. Additionally, the attenuation CT data were acquired right after the SPECT scans with 120 kVp and 20 mAs and then converted to attenuation maps corresponding to 140 keV with a voxel size of 6.8× 6.8×6.8 mm$^3$ using the scanner software. The attenuation maps were in the unit of cm$^{-1}$. The CT-based attenuation maps and the SPECT images were manually registered using the scanner software.

To evaluate our proposed approach, the Attenuation Corrected (AC) SPECT image reconstruction from the scanner using the CT attenuation map was obtained and used as the ground truth. The bull's-eye polar map was compared between the two kinds of AC SPECT images. The normalized mean square error (NMSE) for the left ventricular myocardium between our proposed offline AC SPECT using deep learning generated attenuation and the scanner AC SPECT images using CT-based attenuation map were compared.

B. Results

Figure 11:
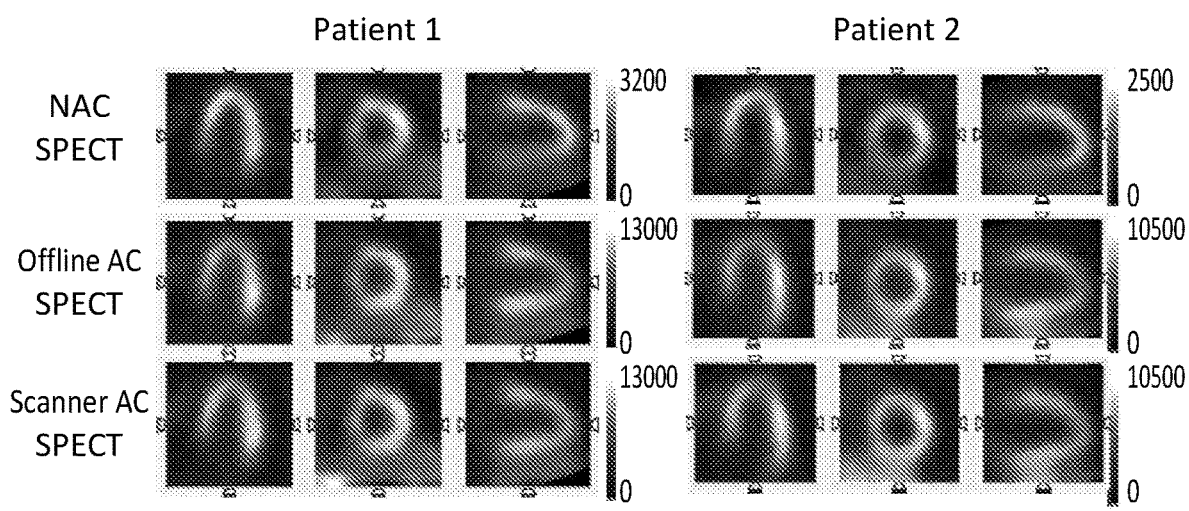
FIG. 11 shows sample slices of two patients for NAC SPECT image, offline AC SPECT image, and scanner AC SPECT image.
Figure 12:
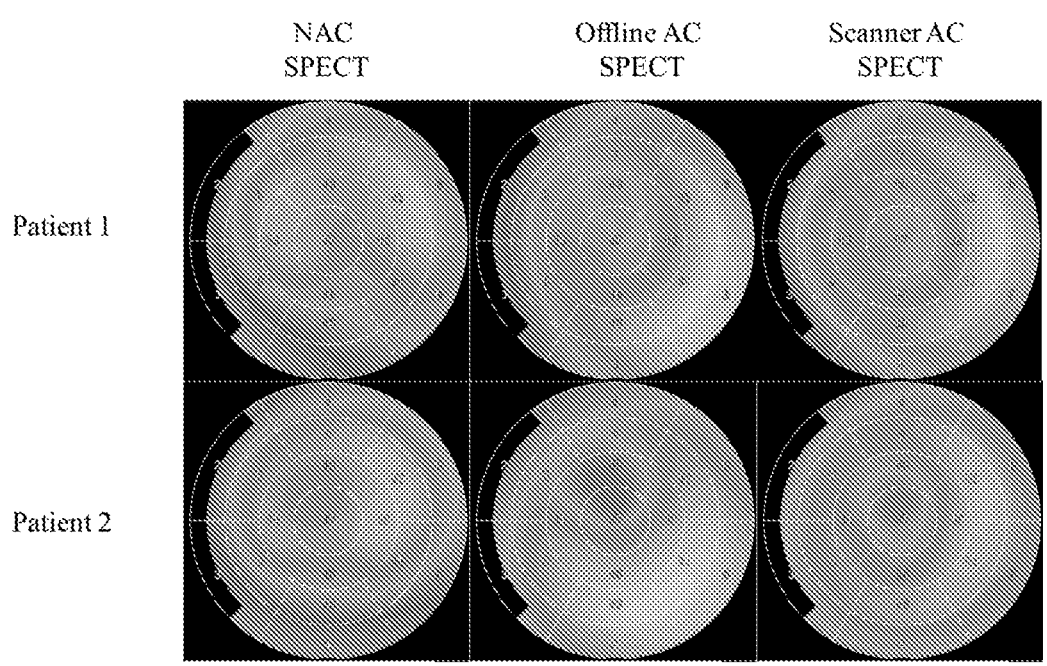
FIG. 12 shows bull's-eye polar maps of two patients derived from NAC SPECT image, offline AC SPECT image, and scanner AC SPECT image.

As shown in FIGS. 11 and 12, the offline AC SPECT images were highly consistent with the scanner AC images. Accordingly, the preceding approach can perform offline attenuation correction based on NAC SPECT images and deep learning generated attenuation map and obtain AC SPECT images consistent with the conventional AC SPECT image using CT attenuation maps. The approach can be applied in most of SPECT images and there is no need to obtain the original emission projection data and the system matrix for the scanner, and no need to access to and integrate with vendor or third party reconstruction software.

III. Conclusion

Through the use of the disclosed embodiments, deep neural networks are used to estimate attenuation coefficients and attenuation corrected images from only the SPECT emission data. Both photopeak and scatter photons are used to help estimate attenuation maps. Using only photopeak photons or only scatter photons can also provide reasonable attenuation map generation using proper neural networks, though using both photopeak and scatter photons provided the most satisfactory results. The disclosed method is fast and can produce realistic attenuation maps with high accuracy. It is also applicable to both specific and non-specific tracers. With the inventive approach, hospitals might not need to purchase hybrid SPECT/CT systems with the additional cost of CT (~1M cost) and lead shielding for the scanning room (another ~1M cost). They will only need to purchase SPECT-only systems. And existing SPECT-only scanners will be able to provide attenuation corrected SPECT images using the inventive approach.

Evaluation on real patient studies shows that use of the disclosed embodiments can produce attenuation maps that are consistent with CT-based attenuation maps, and are able to provide accurate attenuation correction. This development could have a direct benefit to studies acquired on SPECT-only scanners used in clinical practice by providing attenuation correction even without transmission CT data that are only available for hybrid SPECT/CT scanners.

It has been shown that for both the GAN and U-net model, the use of both primary and scatter windows as inputs provided more accurate and robust results compared with using only one energy window input, though GAN is preferred with slightly lower bias. If only the primary window data are used as input, the GAN model was still able to provide reliable attenuation maps, while the U-net model led to much larger bias. In the routine clinical practice, the scatter window data are not always acquired. In this case with only primary window data available, it is still feasible to generate accurate attenuation maps using the GAN model, but not with U-net. On the other hand, for systems with listmode rebinning flexibility, multiple down scatter windows can be generated. Incorporating such multiple scatter windows in combination with primary window data might provide additional benefit and requires further investigation.

In the evaluation example, all the training and testing datasets are myocardial perfusion SPECT studies using $^{99m}$Tc-tetrofosmin. For other tracers, such as $^{99m}$Tc-sestamibi, additional training might be needed to adapt to different tracers, though we expect the tetrofosmin-trained network might still be effective for sestamibi studies due to the similarity of tracer distribution. Although the examples provided with this disclosure focused on the development and evaluation of myocardial perfusion SPECT tracers, the same approach can also be applied to SPECT tracers and studies for other organs in the body and brain, though additional training datasets might be needed to generate appropriate networks for various combinations of organs and tracers. Such additional training studies might also be needed for the SPECT emission images reconstructed with various different methods and parameters, acquired with various injection doses and acquisition times, and different scanners, particularly those using new solid-state detectors.

It has also been found that patient BMI does not affect the performance of the proposed method. However, the methodology of the disclosed embodiments produces slightly higher bias on female subjects compared with male subjects, although the biases on female subjects are still very small (less than 2.6%). This might be caused by the anatomical difference between female and male.

A potential limitation involves the field-of-view (FOV) of SPECT scanners. Since the attenuation maps are generated from the reconstructed SPECT emission images, if the SPECT images are truncated for larger patients with limited SPECT FOV, the truncated region could not be easily recovered. As a result, the generated attenuation maps might also be truncated, which could subsequently affect the accuracy of attenuation correction. This limited FOV issue is particularly challenging for some dedicated cardiac SPECT scanners with limited FOV around the heart without the capability of reconstructing the emission images for the entire body [Wu J, Liu C. Recent advances in cardiac SPECT instrumentation and imaging methods. Physics in Medicine & Biology. 2019; 64:06TR1]. For such systems, an alternate strategy could use deep learning methods to directly convert SPECT images without attenuation correction to images with attenuation correction, as such methods of direct conversion do not require the information of the entire body, though they might require a substantially larger amount of training datasets.

As described above, generating accurate attenuation maps from emission data is feasible for SPECT imaging.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A system for estimating attenuation coefficients or attenuation maps (ATTMAP) from only single photon emission computed tomography (SPECT) emission data using artificial neural networks, comprising:
    a machine learning system based upon deep artificial neural networks for estimating attenuation maps for SPECT emission data consisting essentially of images reconstructed from a photopeak window and/or one or more scatter windows, without requiring additional computed tomography (CT) or other transmission images, the machine learning system both generates attenuation map images from the SPECT emission data, wherein images reconstructed from the photopeak window and/or the scatter window are concatenated/used as a multi-channel/single-channel image, and enforces output attenuation map images to be consistent with a ground truth attenuation map generated based upon empirical evidence.

2. The system according to claim 1, wherein the machine learning system includes a generator network and a discriminator network, the generator network generates attenuation map images from the SPECT emission data, wherein images reconstructed from the photopeak window and/or the scatter window are concatenated/used as a multi-channel/single-channel image and fed into the generator network, and the discriminator enforces output attenuation map images of the generator network to be consistent with the ground truth attenuation map generated based upon empirical evidence.

3. The system according to claim 2, wherein the generator network is trained.

4. The system according to claim 3, wherein the generator network is trained with Generative Adversarial Network training.

5. The system according to claim 3, wherein the generator network is trained with an Adam optimizer.

6. The system according to claim 2, wherein the discriminator network is trained.

7. The system according to claim 6, wherein the discriminator network is trained with an Adam optimizer.

8. The system according to claim 2, wherein the generator network is a deep convolutional neural network.

9. The system according to claim 8, wherein the discriminator network is a deep convolutional neural network.

10. The system according to claim 2, wherein the discriminator network is a deep convolutional neural network.

11. A method for generating attenuation maps and performing associated attenuation correction from SPECT emission data consisting essentially of images reconstructed from a photopeak window and/or one or more scatter windows, without requiring additional computed tomography (CT) or other transmission images, comprising:
    generating an attenuation map from a NAC SPECT image dataset, comprising images reconstructed from the photopeak window and/or the scatter window, through deep learning, wherein generating is performed using a machine learning system that both generates attenuation map images from the SPECT emission data and enforces output attenuation map images;
    estimating attenuated projection data via forward projecting the NAC SPECT image without the attenuation map to create estimated attenuated projection data; and
    reconstructing an AC SPECT image from the estimated attenuated projection data using iterative reconstruction with attenuation correction by incorporating the attenuation map generated by deep learning.

12. The method according to claim 11, where the machine learning system is based upon artificial neural networks.

13. The method according to claim 12, wherein the artificial neural network includes a generator network.

14. The method according to claim 13, wherein the generator network is a deep convolutional neural network.

* * * * *